(12) United States Patent
Kumar et al.

(10) Patent No.: US 11,123,574 B2
(45) Date of Patent: Sep. 21, 2021

(54) ESTIMATION OF THE ACHIEVABILITY OF TREATMENT GOALS IN RADIATION THERAPY

(71) Applicant: KONINKLIJKE PHILIPS N.V., Eindhoven (NL)

(72) Inventors: Prashant Kumar, Bangalore (IN); Vaitheeswaran Ranganathan, Bangalore (IN)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 131 days.

(21) Appl. No.: 16/481,101

(22) PCT Filed: Jan. 30, 2018

(86) PCT No.: PCT/EP2018/052316
§ 371 (c)(1),
(2) Date: Jul. 26, 2019

(87) PCT Pub. No.: WO2018/138387
PCT Pub. Date: Aug. 2, 2018

(65) Prior Publication Data
US 2019/0388708 A1 Dec. 26, 2019

(30) Foreign Application Priority Data
Jan. 30, 2017 (EP) .................................. 17153731

(51) Int. Cl.
*A61N 5/10* (2006.01)
(52) U.S. Cl.
CPC .......... *A61N 5/1031* (2013.01); *A61N 5/1045* (2013.01)

(58) Field of Classification Search
CPC ..... A61N 5/103; A61N 5/1045; A61N 5/1031
See application file for complete search history.

(56) References Cited

U.S. PATENT DOCUMENTS

2015/0087879 A1* 3/2015 Nelms .................. A61B 6/5294
600/1
2015/0141733 A1 5/2015 Kumar

FOREIGN PATENT DOCUMENTS

WO 2014068435 A2 5/2014
WO 2016081916 A1 5/2016

OTHER PUBLICATIONS

Reese Adam et al: "Integral dose conservation in radiotherapy", Medical Physics, AIP, Melville, NY, US, (Year: 2009).*

(Continued)

*Primary Examiner* — Christine H Matthews
*Assistant Examiner* — Joshua Daryl D Lannu

(57) ABSTRACT

In order to assess the achievability of treatment goals for a radiation therapy treatment, an estimation unit generates a treatment plan for the radiation therapy treatment only on the basis of treatment goals relating to a target structure to obtain a first dose distribution, (i) segments the region of the patient's body into a plurality of concentric shells surrounding the target structure and determines a mean radiation dose assigned to each shell in accordance with the first dose distribution, and (iii) checks whether a further dose distribution can be determined, which fulfills the treatment goals relating to at least one structure at risk and, which is configured such that the mean radiation dose assigned to each shell in accordance with the further dose distribution corresponds to the mean radiation dose assigned to the same shell in accordance with the first dose distribution.

20 Claims, 2 Drawing Sheets

(56) References Cited

OTHER PUBLICATIONS

International Search Report and Written Opinion for PCT/EP2018/052316, dated May 14, 2018.
Reese, Adam S. et al "Integral Dose Conservation in Radiotherapy", Medical Physics, vol. 36, No. 3, Mar. 2009, pp. 734-740.

* cited by examiner

ESTIMATION OF THE ACHIEVABILITY OF TREATMENT GOALS IN RADIATION THERAPY

FIELD OF THE INVENTION

The invention generally relates to a planning of an external beam radiation therapy treatment of a patient. More specifically, the invention relates to a system, a method and a computer program for assisting in planning a radiation therapy treatment for a patient.

BACKGROUND OF THE INVENTION

In external beam radiation therapy, ionizing radiation is applied to target structures, such as tumors, within patients' bodies in order to control growth of or kill cancer cells. In advanced types of external beam radiation therapy, such as intensity-modulated radiation therapy (IMRT), defined pre-specified doses of radiation are applied to regions of the patient's body. In this respect, it is typically the goal to deliver a sufficiently high radiation dose to the target structure and to spare sensitive structures, which are usually also referred to as organs at risk, in the vicinity of the target structure as far as possible.

The treatment parameters for delivering the radiation and controlling the radiation treatment device are defined in a treatment plan, which is generated in a planning system. In particular, a so-called inverse planning procedure may be carried out by means of the planning system. In such a procedure, the target structure and the surrounding structures to be spared are identified and treatment goals are specified for these structures. Such treatment goals may correspond to requirements for the radiation dose delivered to certain regions of the patient, such as a maximum or minimum dose to be delivered to a respective region. Then, an optimization process is carried out to find the treatment plan which fulfills the specified treatment goals.

According to one approach for finding the treatment plan, an operator-guided iterative optimization procedure is carried out in the planning system. In this procedure, the optimization of the treatment plan is made in several optimization cycles and after each optimization cycle the treatment planner (typically a physician) may review the treatment plan as calculated in the respective cycle in order to check whether he is satisfied with the dose distribution resulting from this treatment plan. If this is not the case, the planner may modify the treatment goals in order to achieve a desired dose distribution, and the calculation of the treatment plan may be carried out on the basis of the modified treatment goals in the next optimization cycle. This corresponds to a kind of "trial-and-error" approach for finding the best treatment plan.

Using this approach, it is usually possible to find a treatment plan fulfilling the treatment goals with respect to the target structure, which usually include requirements for the minimum dose to be delivered to the target structure and/or parts thereof. However, the delivery of a certain minimum radiation dose to the target structure also results in a certain minimum amount of radiation delivered to the organs at risk surrounding the target structure. Therefore, it is often not possible to find a treatment plan which also fulfills all treatment goals with respect to the organs at risk. As consequence, it is often necessary to make compromises between the treatment goals relating to the target structure and the organs at risk. Sometimes, the best treatment plan may even miss the treatment goals for the organs at risk to such an extent that the treatment can not be carried out for a particular patient without serious health risks.

In this respect, it is a disadvantage of the aforementioned iterative approach that the treatment planner can determine the achievability of the treatment goals only at the end of the iterative optimization procedure, which is a relatively time-consuming process.

SUMMARY OF THE INVENTION

It is an object of the present invention to allow for a prediction of the achievability of treatment goals for a radiation therapy treatment of a patient, particularly of treatment goals relating to organs at risk.

In accordance with a first aspect, the invention suggests a system for assisting in planning a radiation therapy treatment of a region of a patient body on the basis of treatment goals comprising requirements for a radiation dose to be delivered to a target structure and to at least one structure at risk included in the body region. The system comprises an estimation unit configured to:

generate a treatment plan for the radiation therapy treatment only on the basis of the treatment goals relating to the target structure and to obtain a first dose distribution corresponding to the treatment plan, segment the body region into a plurality of concentric shells surrounding the target structure and to determine a mean radiation dose assigned to each shell in accordance with the first dose distribution, check whether a further dose distribution can be determined which fulfills the treatment goals relating to the at least one structure at risk and which is configured such that the mean radiation dose assigned to each shell in accordance with the further dose distribution corresponds to the mean radiation dose assigned to the same shell in accordance with the first dose distribution, and indicate on the basis of a result of the check whether the treatment goals relating to the at least one target structure are achievable.

The invention is based on the finding that the normalized integral shell dose is constant across concentric shells surrounding the target structure when the dose assigned to organs at risk surrounding the target structure is reduced in the generation of a treatment plan for a radiation therapy treatment. In accordance with the invention, this finding is applied to estimate whether the treatment goals relating to the at least one structure at risk are achievable. Hereby, the achievability of the treatment goals relating to the at least one structure at risk can be determined quickly and with a relatively low computational complexity prior to the execution of the complex optimization procedure for determining a treatment plan for the radiation therapy treatment.

In one embodiment of the invention, the system is configured to indicate the achievability of a treatment goal relating to the at least one structure at risk if the check whether the further dose distribution can be determined is affirmative. In a further embodiment of the invention, the estimation unit is configured to carry out said check by executing a procedure for solving an optimization problem for determining the further dose distribution, wherein said check is affirmative if the execution of the procedure results in the determination of the further dose distribution. On the other hand, the check is not affirmative if no solution to the optimization problem can be found by means of the procedure.

Moreover, the estimation unit is preferably configured to generate the first dose distribution on the basis of a three-dimensional image of the body region composed of a plurality of voxels. In this image, the target structure and the at least one structure at risk may be delineated so that voxels belonging to the target structure and the at least one structure at risk can be identified. In the process of determining the first dose distribution, the estimation unit may particularly assign dose values to the voxels belonging to the target structure on the basis of the treatment goals relating to the target structure.

In one embodiment, the estimation unit is configured to check whether the further dose distribution can be determined such that it includes dose values for voxels belonging to the at least one structure at risk, which dose values do not exceed maximum dose values assigned to these voxels on the basis of the treatment goals relating to the at least one structure at risk. By assigning maximum dose values to these voxels, an optimization problem for determining the further dose distribution can be formulated, which involves a relatively low complexity. Thus, the check whether the further dose distribution can be determined requires a relatively short computing time.

In one embodiment of the invention, the estimation unit is configured to check whether the further dose distribution can be determined such that it includes dose values for voxels not belonging to the target structure or the at least one structure at risk, which dose values do not exceed maximum dose values assigned to these voxels. This embodiment takes account of the fact that it is often desired that the radiation dose, which is delivered to regions of the patient not belonging to target structure or a structure at risk, is kept below certain values in order to avoid necrosis in such regions.

In a related embodiment of the invention, the maximum dose value assigned to a voxel is determined on the basis of a desired difference between the radiation dose assigned to the voxel and the radiation dose assigned to the target structure in accordance with the first dose distribution, the desired difference being determined on the basis of a predetermined dose fall-off gradient. The predetermined dose fall-off gradient may be specified by an operator of the system. As an alternative, the predetermined dose fall-off gradient may be pre-stored in the estimation unit. In this case, the pre-stored value may correspond to a dose fall-off gradient which is typically realizable in the radiation therapy system used to deliver the radiation therapy treatment.

In a further embodiment of the invention, the estimation unit is configured to carry out said check whether the further dose distribution can be determined by executing a procedure for solving an optimization problem for determining the further dose distribution on the basis of a second dose distribution, the second dose distribution assigning a dose value to each voxel not belonging to the target structure, which dose value is determined on the basis of the dose fall-off gradient.

In this embodiment, the estimation unit may particularly try to determine the further dose distribution starting from the second distribution in order to carry out said check. In so doing, the estimation unit may effectively try to reduce dose values assigned to voxels belonging to the at least one structure at risk and to compensate the reduction by increasing dose values assigned to voxels not belonging to the at least one structure at risk or the target structure in such a way that the mean shell doses correspond to the mean shell doses of the first dose distribution. In this process, the increase of the dose values assigned to voxels not belonging to the at least one structure at risk or the target structure may further be limited by a predetermined threshold. Hereby, it can be achieved that these dose values do not exceed maximum values determined on the basis of the dose fall-off gradient.

In one embodiment of the invention, the estimation unit is configured to determine the first dose distribution such that the radiation dose assigned to the target structure at least approximately corresponds to a minimum radiation dose required for fulfilling the treatment goals relating to the target structure. In such a way, also the treatment plan for delivering a radiation treatment is usually generated in order to minimize the radiation dose delivered to the structures at risk.

In a further embodiment of the invention, the estimation unit is configured to determine minimum dose values for voxels belonging to the at least one structure at risk if the check whether the further dose distribution fulfilling the treatment goals can be determined is not affirmative, which minimum dose values allow for determining a dose distribution such that the mean radiation dose assigned to each shell in accordance with the further dose distribution corresponds to the mean radiation dose assigned to the same shell in accordance with the first dose distribution. On the basis of the minimum dose values, the treatment goals relating to the at least one structure at risk may be modified such that they are achievable.

In a related embodiment of the invention, the minimum dose values additionally allow for determining the dose distribution such that it includes dose values for voxels not belonging to the target structure or the at least one structure at risk, which dose values do not exceed maximum dose values assigned to these voxels. These maximum dose values may again be determined on the basis of desired differences between the radiation doses assigned to these voxels and the radiation dose assigned to the target structure in accordance with the first dose distribution as explained above.

In accordance with a further aspect, the invention suggests a method for assisting in planning a radiation therapy treatment of a region of a patient body on the basis of treatment goals comprising requirements for a radiation dose to be delivered to a target structure and to at least one structure at risk included in the body region. The method comprises:

generating a treatment plan for the radiation therapy treatment only on the basis of the treatment goals relating to the target structure and obtaining a first dose distribution corresponding to the treatment plan, the treatment plan specifying optimized parameters for delivering the radiation treatment, segmenting the body region into a plurality of concentric shells surrounding the target structure and determining a mean radiation dose assigned to each shell in accordance with the first dose distribution, checking whether a further dose distribution can be determined which fulfills the treatment goals relating to the at least one structure at risk and which is configured such that the mean shell dose assigned to each shell in accordance with the further dose distribution corresponds to the mean radiation dose assigned to the same shell in accordance with the first dose distribution, and indicating on the basis of a result of the check whether the treatment goals relating to the at least one target structure are achievable.

In accordance with a further aspect, the invention suggests a computer program executable in a processing unit of a system for assisting in planning a radiation therapy treatment, the computer program comprising program code means for causing the processing unit to carry out the method.

It shall be understood that the system of claim 1, the method of claim 14 and the computer program claim 15 have similar and/or identical preferred embodiments, in particular, as defined in the dependent claims.

It shall be understood that a preferred embodiment of the present invention can also be any combination of the dependent claims or above embodiments with the respective independent claim.

These and other aspects of the invention will be apparent from and elucidated with reference to the embodiments described hereinafter.

DETAILED DESCRIPTION OF EMBODIMENTS

The invention relates to the planning of an external beam radiation therapy treatment of a target structure in a body of a patient. The target structure may particularly be a tumor and the treatment may be carried out in order to kill or control growth of cancer cells of the tumor. For controlling the treatment equipment, such as the radiation source, during the delivery of the treatment, a treatment plan is used which specifies the relevant parameters for controlling the treatment equipment and it is an aim of the planning process to generate the treatment plan for a specific treatment.

Figure 1:
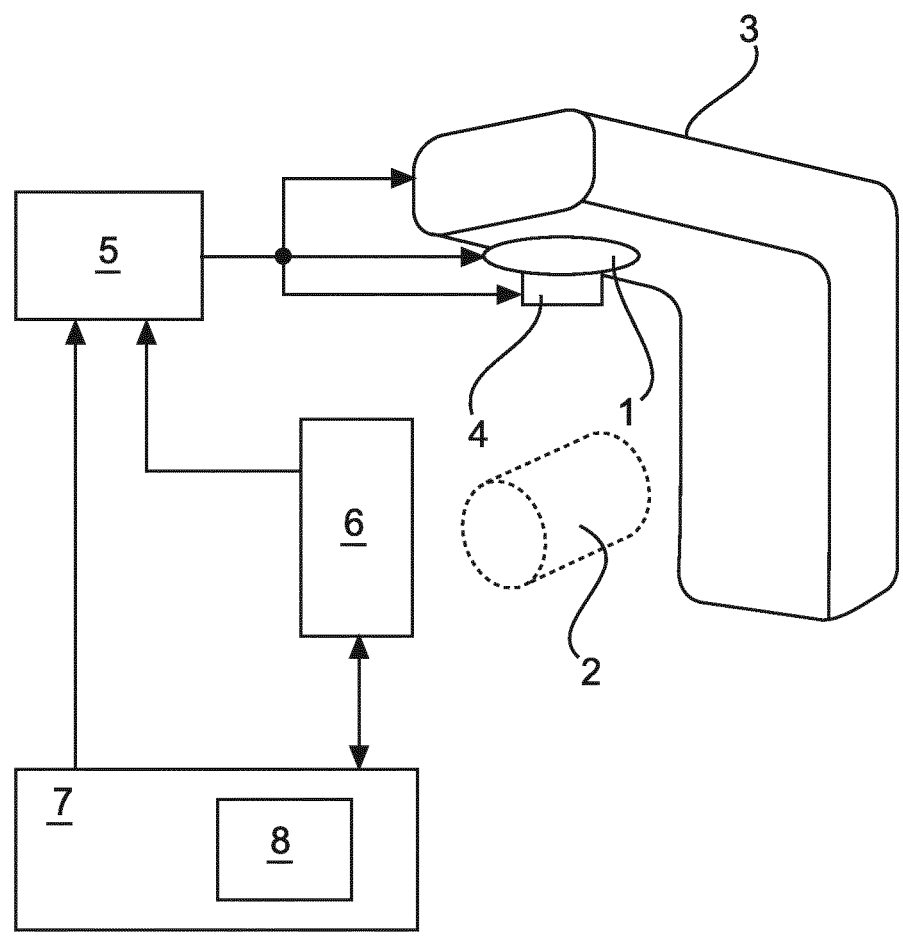
FIG. 1 schematically and exemplarily shows a radiation therapy system including a planning unit for generating a treatment plan, FIG. 2 schematically and exemplarily shows steps of an estimation routine for checking the achievability of treatment goals relating to organs at risk, and FIG. 3 schematically and exemplarily shows and target structure and dose shells surrounding the target structure.

FIG. 1 schematically and exemplarily illustrates an embodiment of a radiation therapy system for delivering an external beam radiation treatment. In this embodiment, the radiation therapy system comprises a radiation source 1, which can be operated to emit ionizing radiation to be delivered to a patient body positioned in a treatment zone 2. For supporting the patient body within the treatment zone 2, the system may comprise a patient table. The relative position and orientation of the radiation source 1 with respect to the patient body can be varied over a certain range of positions and orientations. For this purpose, the radiation source 1 may be mounted on rotatable gantry 3 so that the radiation source 1 can be rotated around the treatment zone or body within a certain angular range, which may be 360° or less. In addition, the gantry 3 and/or the patient table may be movable back and forth in a direction parallel to the rotation axis of the gantry 3. Further, it may also be possible to rotate the patient table around an axis perpendicular to the rotation axis of the gantry 3.

The radiation source 1 may include an x-ray tube or a linear particle accelerator for producing at least one ionizing radiation beam. The radiation source 1 is controllable in order to vary the intensity and/or energy of the radiation beam. Further, the radiation source 1 may be provided with a collimator 4 for shaping the radiation beam. The collimator 4 may particularly allow varying the radiation intensity across the radiation beam in a defined way. For this purpose, the collimator 4 may be configured as a multi-leaf collimator. Such a collimator may comprise a plurality of leaves which can be moved independently in and out of the path of a particle beam in order to shape the beam.

During delivery of the radiation treatment, the configuration of the radiation source 1 and/or the collimator 4 is usually varied based on the treatment plan discussed herein below so that the radiation beam is delivered with a time-varying shape. In one related implementation, the radiation treatment is delivered in accordance with successive segments, where each segment corresponds to a certain collimator configuration or beam shape and to certain emitted radiation dose, which may be specified in monitor units (MU). In between two segments, the collimator configuration may be changed from the configuration of the first segment to the configuration of the second segment, and, during this period, the radiation beam may be turned off. This approach is usually also referred to as step-and-shoot approach. Likewise, it is possible to continuously change the collimator configuration and/or the emitted dose in accordance with the segments without interrupting the radiation beam, as it is the case in volume modulated arc therapy (VMAT), for example.

For controlling the radiation source 1, the collimator 4 and the patient table during the treatment—particularly for controlling the modifiable parameters of the radiation source 1, the collimator 4 and the patient table—the system includes a control unit 5. During a radiation treatment, the control unit 5 controls the relative position and orientation of the radiation source 1 and the body by positioning the gantry 3 and/or the patient table. Further, the control unit 5 controls the intensity and energy of the radiation beam and the radiation beam shape. Preferably, the control unit 5 is implemented in a processor unit including a microprocessor for executing a control program comprising the control routines carried out by the control unit 5.

In addition, the radiation therapy system may comprise or be coupled to an imaging unit 6 for imaging a region of interest of the patient body, which particularly includes the target structure. The imaging unit 6 may be capable of acquiring three-dimensional images and may include an ultrasound device, a computed tomography (CT) device or a magnetic resonance imaging (MRI) device, for example. Using the imaging unit 6, images of the body region of interest may be acquired in advance and/or during the during the radiation treatment. On the basis of these images, the patient body may be positioned for the treatment and/or the treatment may be adapted to changes of the target structure and/or surrounding tissue during the treatment, for example.

The radiation treatment may be delivered during one or more fraction(s), where individual fractions may be delivered on consecutive days or in another cycle. In order to deliver one fraction, the patient body is positioned in the treatment zone 2 of the radiation therapy system at a defined position relative to the radiation source 1. Thereupon, the control unit 5 controls the delivery of radiation to the structure to be treated. In so doing, the control unit 5 aligns the radiation source 1 and controls the further parameters of the radiation source 1 and the collimator 4 in accordance with a treatment plan stored in the control unit 5 for the treatment of the specific patient. As said above, the treatment plan defines the irradiation parameters for the radiation treatment. These parameters particularly include the alignment of the radiation source 1 relative to the target region within the patient body, the collimator configurations to be used during the treatment and the radiation intensities.

For planning the radiation treatment, the radiation therapy system comprises a planning unit 7. The planning unit 7 may be configured as a computer device, such as, for example a personal computer, which executes a planning software for generating treatment plans which are then used by the control unit 5 for controlling the execution of the treatment fractions. The planning process is preferably made under the control of a treatment planner operating the planning unit 7 using a planning image of the body region of interest, which is also referred to as planning volume herein below. The planning image may be acquired using the imaging unit 6 integrated into the radiation therapy system or using another imaging unit. In the planning image, structures relevant for the radiation treatment are delineated using a suitable delineation procedure. The relevant structures include the target structure and sensitive structures surrounding the target structure, which are referred to as organs at risk (OARs) herein. For delineating the target structure and the OARs any suitable delineation procedure known to the person skilled in the art may be used including an automatic delineation, a semi-automatic delineation or a manual delineation in which an operator inputs the counter of the target structure using a suitable input means, such as, for example, a computer mouse.

The planning of the treatment is carried out on the basis of treatment goals which may particularly specify a radiation dose to be delivered to the target structure. This treatment goal may be specified in a clinical prescription for the patient, which is prepared on the basis of a clinical diagnosis preceding the radiation therapy treatment. In addition, the treatment goals specify requirements for the radiation dose delivered to OARs. These treatment goals may likewise be included in the prescription for the patient, or they may be specified in general rules relating to the radiation treatment.

The treatment goals generally correspond to hard or soft constraints corresponding to requirements for the radiation dose delivered to certain regions of the region of interest of the patient body. Hard constraints correspond to requirements that must be fulfilled and soft constraints correspond to requirements that should be fulfilled. Possible constraints particularly comprise maximum and minimum dose constraints specifying a maximum or minimum radiation dose to be delivered to certain voxel(s) of the planning volume. In addition, it may be possible to specify that that a certain region receives a uniform radiation dose (so-called uniform dose constraint) or that a certain region receives a specified mean dose value (so-called mean dose constraint). Further, possible constraints comprise maximum and minimum mean dose constraints specifying that a maximum or minimum mean dose is delivered to a certain region of the planning volume. Such constraints are also referred to as Max DVH or Min DVH constraints (DHV: Dose Volume Histogram).

The treatment goals relating to the OARs are typically specified using maximum dose constraints and/or Max DVH constraints since it is typically desired that the radiation dose delivered to the OARs does not exceed prescribed thresholds. The treatment goals relating to the target structure are typically specified using particularly minimum dose constraints, which may be combined with maximum dose constraints and/or uniform dose constraints. Using such constraints, it can be ensured that the target structure receives a prescribed dose and that neither under dosage (so-called cold spots) nor over-dosage (so-called hot spots) occurs.

In order to generate a treatment plan for controlling the treatment of a particular patient, an optimization problem is formulated on the basis of the hard and soft constraints specified for the patient with respect to the relevant planning volume. The planning unit 7 then tries to at least approximately solve the optimization problem. This means that the planning unit tries to determine a treatment plan which corresponds to a dose distribution fulfilling the constraints, where the dose distribution corresponds to the spatial distribution of the radiation dose values in the planning volume. In order to try to find such a treatment plan, an operator-guided iterative optimization procedure may be applied in which the planner may modify the treatment goals and/or other parameter of the calculation in order to arrive at the optimum treatment plan. In each step of this procedure, the planning unit 7 automatically calculates a preliminary treatment plan by approximating a solution of the optimization problem. Then, the plan unit 7 determines the dose distribution corresponding to this treatment plan and visualizes the dose distribution to the planner operating the planning unit 7. The planner reviews the dose distribution to decide whether he/she is satisfied with the dose distribution or not. If the user is satisfied in one step, the treatment plan calculated in this step is used as the final treatment plan. If the user is not satisfied, the optimization problem is modified in accordance with changes specified by the user as a result of his/her review. Then, the planning unit 7 calculates a new preliminary treatment plan in the next iteration step.

The optimization problem to be solved may correspond to the minimization of a cost function F formulated on the basis of the treatment goals. The cost function F may comprise a collection of individual objective functions $F^k$, where each individual objective function $F^k$ represents one soft constraint. In one embodiment, the cost function F may particularly correspond to a weighted sum of the objective functions $F^k$, i.e.

$$F(\tau) = \sum_{k=1}^{N} w^k F^k,$$

where τ represents the set of treatment parameters to be determined (as will be explained herein below) and the parameters $w^k$ denote weights of the objective functions $F^k$. Due to the weighting, soft constraints having a higher weight are satisfied more likely than soft constraints having a lower weight, in case such constraints are in conflict with each other. Hence, the weights are selected in accordance with the importance of the soft constraints with respect to the success of the treatment.

As an example, the objective function representing a maximum/minimum dose soft constraint for the radiation dose for a certain volume V may be given by $$F^k = \sum_{i \in V} f(d_i, d^k) \cdot \left[ \frac{d_i - d^k}{d^k} \right]^2 \cdot \Delta v_i,$$

where $f(d_i, d^k) = H(d_i - d^k)$ in case a maximum dose is specified and $f(d_i, d^k) = d_i(\tau)$ in case a minimum dose is specified. $\Delta v_i$ denotes the volume of the voxel i, $d_i = d_i(\tau)$ is the radiation dose delivered to the voxel i when the irradiation parameters τ are used, $d^k$ is the maximum/minimum radiation dose to be delivered to the volume V, and H is the Heaviside step function defined by $$H(x) = \begin{cases} 0, & x < 0 \\ 1, & x \geq 0 \end{cases}.$$

Each hard constraint may be represented by a function $C(\tau)$ so that the planning unit 7 may minimize the aforementioned function $F(\tau)$ and may at the same time ensure that $$C(\tau) \geq 0 \text{ or } C(\tau) = 0$$

is fulfilled. For instance, the corresponding function C for a hard constraint corresponding to a maximum dose requirement may be $C = d^k - d_i$ and the function C for a constraint corresponding to a minimum dose requirement may be $C = d_i - d^k$.

By minimizing the cost function, an optimized vector r can be determined which represents the treatment parameters for the treatment plan to be generated.

In one embodiment, the radiation beam is modeled as a set of small beam elements, where the beam elements may be defined on the basis of a predetermined grid dividing the beam's cross section into sections corresponding to the beam elements. In this embodiment, the vector $\tau$ may specify radiation fluences for the individual beam elements and the dose function $d_i$ may be configured as a function of these fluences, where the fluence corresponds to the integrated flux of radiation. On the basis of fluences obtained as a solution to the optimization problem, the planning unit 7 may then determine the actual treatment parameters, such as the configuration parameters for the radiation source 1 and the collimator 4, which are also referred to as machine parameters.

In a further embodiment, the vector $\tau$ specifies the machine parameters. This means that the dose function $d_i$ may be configured as a function of the machine parameters rather than the fluences. In this embodiment, optimized machine parameters are directly determined as a solution of the optimization problem. Therefore, implementations of this embodiment are also referred to as direct machine parameter optimization (DPMO).

In order to determine the treatment parameters such that the objective function is (approximately) minimized and the hard constraints are fulfilled, the planning unit 7 may apply any suitable optimization algorithm known to the person skilled in the art. The optimization algorithm may in itself be an (automatic) iterative procedure, in which an optimum solution is calculated starting from an initial set of treatment parameters. In one exemplary implementation, the planning unit 7 may use the NPSOL algorithm described in P. E. Gill et al., "User's guide for NPSOL 5.0: A Fortran package for nonlinear programming", Technical Report SOL 86-6, Revised 2001. However, any other suitable algorithm known to a person skilled in the art may likewise be used.

Using such an algorithm, the planning unit 7 may calculate a treatment plan in each step of the user-guided optimization procedure explained above. When an iterative algorithm is applied, the initial set of treatment parameters used in the second and each subsequent step may (but not necessarily have to) correspond to the treatment parameters calculated in the preceding step. In the first step, the initial set of treatment parameters may be determined using a suitable heuristic. Moreover, as said above, the optimization problem may be modified in accordance with changes specified by the planner in the second and each subsequent step of the procedure, when the planner is not satisfied with the dose distribution resulting from the generated treatment plan. Possible changes comprise the modification of soft and/or hard constraints and the adaption of weights of the objective functions representing the soft constraints, where a weight adaptation is normally preferred in order to maintain conformance between the constraints and the treatment goals prescribed for the patient.

As already said in the introduction, the determination of the treatment plan in the operator-guided iterative planning procedure is a time-consuming task. Moreover, it is sometimes not possible to calculate an optimum treatment plan fulfilling all treatment goals. This may particularly be due to conflicts between the treatment goals relating to the target structure and treatment goals relating to the OARs. In this case, the planner has to adapt the treatment goals in order to find a compromise between the treatment goals relating to the target structure and the organs at risk during the planning procedure. If such an adaptation is possible, the treatment plan then has to be newly calculated on the basis of the modified treatment goals.

Therefore, the invention particularly provides an estimation routine for assessing the achievability of treatment goals without having to carry out the iterative treatment planning procedure explained above. Hence, the planner can check whether the treatment goals relating to the organs at risk can likewise be achieved in addition to the treatment goals relating to the target structure. If the treatment goals are achievable according to the estimation routine, the estimation routine also allows for determining a dose distribution on the basis of which an set for treatment parameters may be determined, which may be used as an initial set of treatment parameters in the first step of the operator-guided treatment planning procedure explained above.

As will be explained in more detail herein below, the estimation routine is based on the finding described in the publication A. S. Reese et al. "Integral dose conservation in radiation therapy", Med. Phys. 36, (734) 2009, that the normalized integral shell dose is constant across concentric shells surrounding the target structure when the dose assigned to OARs surrounding the target structure is reduced. This means that the normalized integral shell dose, normalized to the average integral shell dose, across concentric shells surrounding the target structure is constant for treatment plans which differ in the radiation dose delivered to the OARs. Hence, the radiation dose in each shell cannot be eliminated but only redistributed in order to spare organs. This implies limitations in the extent to which an OAR can be spared based on the location of the OAR relative to the target structure and based on the geometry of the OAR. Taking into account these limitations, the suggested estimation routine particularly makes it possible to check the achievability of the treatment goals relating to the OARs.

The estimation routine may be carried out by a software-implemented estimation unit 8. In a radiation therapy system configured as described above, the estimation unit 8 may be integrated into the planning unit 7. Likewise, the estimation unit 8 may be implemented in other suitable computer device. This computer device does not necessarily have to be directly included in a radiation therapy system. Rather, a treatment planner or another operator may use a computer device, which is operated independently of a radiation therapy system, in order to execute the estimation routine.

Figure 2:
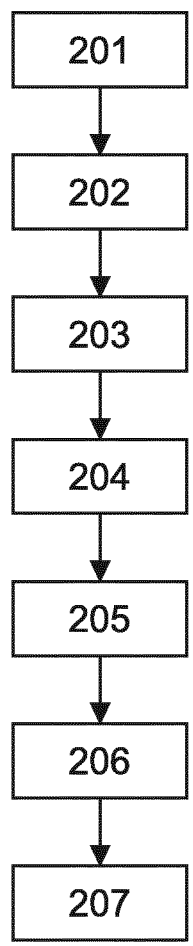

As an example, FIG. 2 illustrates steps which may be carried out in connection with the execution of the estimation routine.

In a first step 201, the estimation unit 8 obtains a planning image of the body region of interest of a patient and the treatment goals relating to the target structure and to the structures at risk included in the body region of interest. In the planning image, particularly the target structure is being delineated by means of the estimation unit 8 (if this has not been done previously).

On the basis of the planning image and the delineation of the target structure therein and on the basis of the treatment goals relating only to the target structure, the estimation unit 8 determines a treatment plan which fulfills these treatment goals in step 202. The treatment plan is determined such that an approximate optimum of the dose distribution in the region of the target structure is achieved. This particularly means that the treatment goals relating to the target structure are fulfilled. Moreover, the radiation dose assigned to the target structure at least approximately corresponds to a minimum radiation dose required for fulfilling the treatment goals relating to the target structure.

The treatment goals relating to the OARs are ignored by the estimation unit 8 when calculating the treatment plan in the aforementioned step. Hence, there are no potentially conflicting treatment goals for the OARs to be taken into consideration in the determination of the treatment plan so that the estimation unit 8 will most probably be able to determine a suitable treatment plan. As said above, conflicts between treatment goals primarily exist between treatment goals relating to the target structure, which typically require a minimum radiation dose to be delivered to the target structure, and treatment goals relating to the OARs, which typically require that the radiation dose delivered to the OARs do not exceed prescribed maximum values. Due to such conflicts it may not be possible to determine a treatment plan fulfilling both the treatment goals relating to the target structure and the treatment goals relating to the OARs. However, if only the treatment goals relating to the target structure are taken into consideration, a treatment plan can usually be determined.

In order to determine the treatment plan on the basis of the treatment goals relating to the target structure in the step 202, the estimation unit 8 may apply any suitable calculation algorithm known to a person skilled in the art. In particular, the estimation unit 8 may minimize a cost function including objective functions corresponding to the individual treatment goals relating to the target structure as described above using a suitable algorithm in order to determine optimized treatment parameters and/or fluences for the individual beam elements of the model of the radiation beam. Embodiments of such an algorithm were already referred to above.

Upon having determined the treatment plan on the basis of the treatment goals relating to the target structure, the estimation unit 8 obtains the corresponding dose distribution within region of the target structure in step 203. This dose distribution, which is also referred to as first dose distribution herein, can be calculated using the treatment parameters of the treatment plan and/or the fluences of the beam elements corresponding to these treatment parameters.

Figure 3:
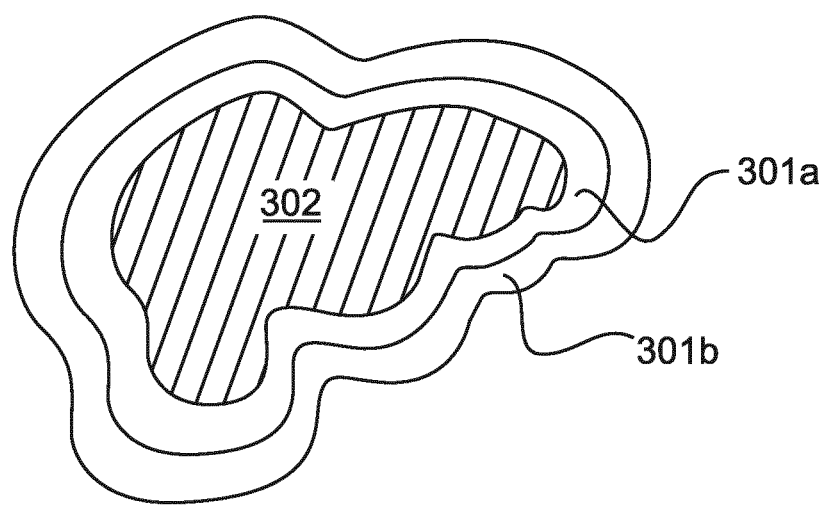

Further, in step 204, the estimation unit 8 segments the planning volume into concentric shells 301a, 301b surrounding the target structure. As schematically and exemplarily illustrated in FIG. 3, the boundaries of these shells 301a, 301b correspond to expanded contours of the target structure 302. The expanded contours have the same shape as the original contour of the target structure 302 and surround the target structure concentrically. Further, the distances between the boundaries of neighboring shells are preferably substantially equal (i.e. the shell boundaries are arranged equidistantly). The number of shells can in principle be selected arbitrarily and may be adapted to the size of the planning region, for example.

The expanded contours of the target structure 302 and the resulting shells can be determined by the estimation unit 8 in any suitable way known to the person skilled in the art. In one implementation, the contours may be determined on the basis of a distance transform. In particular, the estimation unit 8 may determine the distance transform of the voxels of the planning volume outside the target structure, which assigns to each voxel the minimum distance to the target structure. Then the boundaries of the shells are generated such that they contain all voxels to which the distance transform assigned the same predetermined value.

For each shell, the estimation unit 8 determines a mean shell dose value in step 205 for the first dose distribution. For each shell, this value corresponds to an average radiation dose delivered to the voxels of the shell in accordance with the first dose distribution. Upon calculation of the mean shell dose values for the shells, the estimation unit 8 stores the calculated mean dose values in a memory for future use.

Further, the estimation unit 8 may determine a virtual dose distribution for the body region of interest in step 206, which is also referred to as second dose distribution herein. In the region including the target structure, the second dose distribution corresponds to the first dose distribution. For the region surrounding the target structure, the second dose distribution is preferably generated on the basis of a predetermined dose gradient describing a decrease of the radiation dose delivered to the region surrounding the target structure with increasing distance from the target structure. Hereby, account is taken of the fact that usually a certain minimum dose fall-off gradient is desired in addition to the fulfillment of the treatment goals relating to the target structure and the organs at risk. Such a dose fall-off gradient ensures that the radiation dose delivered to regions of patient body, which do not correspond to the target structure or the organs at risk, is minimized or at least reduced.

The gradient value, which is used for determining the second dose distribution, may be specific to the radiation therapy system, particularly for the radiation source 1, used for delivering the radiation therapy and may correspond to typical gradients achieved by means of the radiation therapy system in practice. As an alternative, the operator of the estimation unit 8 may specify a desired and realizable gradient value.

Moreover, the estimation unit 8 accesses the treatment goals relating to the OARs included in the planning unit and assigns maximum dose values to the voxels belonging to the OARs on the basis of these treatment goals in step 207.

In so doing, the estimation unit 8 assigns the specified maximum or the mean dose values to voxels included in regions for which maximum or mean dose values are specified in the treatment goals. If a maximum dose to be delivered to a certain region is specified (Max DVH constraint), the estimation unit 8 assigns a maximum dose value corresponding to the dose goal to voxels included in the respective region until the maximum dose is reached. Thus, if the corresponding constraint specifies that no more than 30% of a certain volume shall receive a dose higher than 45 Gray (Gy), for example, a maximum dose value of 45 Gy is assigned to 30% of the voxels included in the relevant volume. The assignment is preferably carried out in such an order that voxels which are closer to the target structure are linked to the relevant dose value prior to voxels which have a greater distance to the target structure. Hence, the voxels to which no dose value is assigned upon having reached the dose goal are further away from the target structure than the voxels to which a dose value is assigned.

If the treatment goals comprise multiple constraints for certain regions, the assignment is made in a predetermined order. When carrying out multiple assignments in this order, each new assignment replaces or overwrites the previous assignments. In particular, the order may be: (i) Maximum dose constraints, (ii) Mean dose constraints, (iii) Max DVH constraints. Within the same category of constraints, the assignment may be made in the order from higher to lower dose goals. When the assignment is made in this order, it is ensured that the most restrictive dose goal is eventually assigned to each voxel. Minimum dose constraints do not have to appear in the predetermined order, since such constraints are usually not assigned to OARs.

In the next step 208, the estimation unit 8 executes a procedure for solving an optimization problem on the basis of the second dose distribution for determining a third dose distribution, in which the mean shell doses correspond to the mean shell doses determined for the first dose distribution and stored by the estimation unit 8 and in which the maximum dose values assigned to the voxels in the preceding step are not exceeded. Moreover, the allowed increase of the dose value for the remaining voxels to which no maximum dose value was assigned in the previous step compared with dose value for these voxels in accordance with the second dose distribution is preferably limited by a predetermined threshold value.

Starting from the second dose distribution, the estimation unit 8 effectively tries to solve the optimization problem in the executed procedure and to determine the third dose distribution by appropriately reducing the dose value for voxels to which a maximum dose value was assigned in step 207, if necessary (i.e. if the dose value according to the second dose distribution is higher), and by increasing the dose values for other voxels. This is to be done in such a way that the mean shell dose for each shell corresponds to the mean shell dose determined based on the first dose distribution and that the increase of the dose values for the other voxels does not exceed the predetermined threshold.

The computational complexity of this optimization problem is significantly smaller than the computational complexity of the optimization problem for determining the treatment plan on the basis of all treatments goals. Therefore, a solution to this optimization problem can be computed relatively easily and quickly, if such a solution exists.

On the basis of result of the execution of the procedure for solving the optimization problem for determining the third dose distribution, the achievability of the treatment goals relating to the OARs can be predicted. The predication can particularly be made in the following way:

If the estimation unit 8 successfully solves the optimization problem and determines a third dose distribution fulfilling the conditions explained above, it can particularly be assumed that the treatment goals are achievable. In this case, a treatment plan may be generated on the basis of these treatment goals. This may be done in accordance with the operator-guided iterative optimization procedure explained above.

In this procedure, the third dose distribution determined by the estimation unit 8 may be used to determine the starting point. For this purpose, values of the relevant treatment parameters may be determined which lead to the third dose distribution and these values may be used as start values in the user-guided iterative optimization procedure. Since the third dose distribution is determined on the basis of the actual treatment goals, it may provide a relatively good approximation of the dose distribution corresponding to the treatment plan to be determined. Hence, it may be possible to quickly determine a treatment plan in few steps, when the start values of the treatment parameter are generated on the basis of the third dose distribution.

If the estimation unit 8 does not find a solution to the optimization problem, it can be assumed that the treatment goals are not achievable. In this case, the estimation unit 8 may output an indication informing the operator accordingly.

If the treatment goals are not achievable, a modification of the treatment goals relating to the organs at risk is necessary in order to be able to deliver the radiation treatment.

In order to assist the operator in modifying the treatment goals, the estimation unit 8 may determine lower bounds of dose values for voxels belonging to one or more OARs, which allow for solving the optimization problem for determining a third dose distribution fulfilling the aforementioned requirements. For this purpose, the estimation unit 8 may reduce the maximum dose value assigned the voxels belonging to these OARs in step 207 in one or more steps by a predetermined amount and, in each step, the estimation unit 8 may try to solve the optimization problem. Once the optimization problem can be solved in one step, the estimation unit 8 outputs the corresponding reduced values as lower bounds for the dose values of the voxels belonging to the relevant OARs.

The relevant OARs may be selected on the basis of priorities assigned to the treatment goals relating to different OARs and may correspond to those OARs for which treatment goals with a lower priority have been specified. In such a way, the relevant OARs may be selected manually by the operator of the estimation unit 8, or the estimation unit 8 may automatically select the relevant OARs on the basis of priorities assigned to the treatment goals. The priorities may be assigned to the treatment goals on the basis of the clinical importance of the treatment goals for the success of the radiation treatment.

Once the lower bounds for the dose values belonging to the relevant OARs have been determined, the operator can estimate the trade-offs to be made in order to modify the treatment goals such that they are achievable. If these trade-offs are acceptable, the operator may modify the treatment goals relating to the relevant OARs such that the modified treatment goals do not require the dose values of the voxels belonging to the relevant OARs to be smaller than the determined lower bounds.

Thereupon, a treatment plan for the delivering the radiation therapy treatment may be determined on the basis of the modified treatment goals using an operator-guided optimization procedure as explained above. In this procedure, the third dose distribution determined by the estimation unit 8 as a solution to the optimization problem may again be used for obtaining start values of the treatment parameters.

In the way described above, the achievability of treatment goals relating to OARs can be determined prior to the generation of a treatment plan. Further, the embodiments described above allow for determining the achievability of the treatment goals when the radiation dose decreases with increasing distance from the target structure in accordance with a dose fall-off gradient. For this purpose, the estimation unit 8 generates the second dose distribution and tries to find a third dose distribution in which the dose value assigned to each voxel does not differ from the dose value assigned to the voxel in accordance with the second dose distribution by more than a predetermined amount.

In further embodiments, the achievability of the treatment goals is assessed without taking account of a decrease of the radiation dose in accordance with a dose fall-off gradient. In these embodiments, the generation of the second dose distribution is dispensed with and the increase of the dose value for the voxels to which no maximum dose value was assigned in the step 207 is not further limited (i.e. in addition to the requirement that the mean shell dose values for the third dose distribution correspond to those for the first dose distribution). In all other respect, the estimation unit 8 may try to solve an optimization problem as described above in these embodiments.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A system for assisting in planning a radiation therapy treatment of a region of a patient's body on a basis of treatment goals comprising requirements for a radiation dose to be delivered to a target structure and to at least one structure at risk included in the region of the patient's body, the system comprising a computer device and a tangible, non-transitory computer readable storage medium that stores instructions, which when executed by the computer device causes the computer device to:

generate a treatment plan for the radiation therapy treatment only on the basis of the treatment goals relating to the target structure and to obtain a first dose distribution corresponding to the treatment plan;

segment the region of the patient's body into a plurality of concentric shells surrounding the target structure and to determine a mean radiation dose assigned to each shell in accordance with the first dose distribution;

check whether a further dose distribution can be determined which fulfills the treatment goals relating to the at least one structure at risk and which is configured such that the mean radiation dose assigned to each shell in accordance with the further dose distribution corresponds to the mean radiation dose assigned to a same shell in accordance with the first dose distribution; and indicate on a basis of a result of the check whether the treatment goals relating to at least one target structure are achievable.

2. The system as defined in claim 1, wherein the instructions, when executed by the computer device, further cause the computer device to carry out the check by executing a procedure for solving an optimization problem for determining the further dose distribution and wherein the check is affirmative when the execution of the procedure results in the determination of the further dose distribution.

3. The system as defined in claim 1, wherein the instructions, when executed by the computer device, further cause the computer device to indicate an achievability of the treatment goals relating to the at least one structure at risk when the check is affirmative.

4. The system as defined in claim 1, wherein the instructions, when executed by the computer device, further cause the computer device to generate the first dose distribution on a basis of a three-dimensional image of the region of the patient's body composed of a plurality of voxels.

5. The system as defined in claim 4, wherein the instructions, when executed by the computer device, further cause the computer device to check whether the further dose distribution can be determined such that it includes dose values for voxels belonging to the at least one structure at risk, wherein the dose values do not exceed maximum dose values assigned to these voxels on a basis of the treatment goals relating to the at least one structure at risk.

6. The system as defined in claim 4, wherein the instructions, when executed by the computer device, further cause the computer device to check whether the further dose distribution can be determined such that it includes dose values for voxels not belonging to the target structure or the at least one structure at risk, which dose values do not exceed maximum dose values assigned to these voxels.

7. The system as defined in claim 6, wherein the maximum dose values assigned to a voxel is determined on a basis of a desired difference between the radiation dose assigned to the voxel and the radiation dose assigned to the target structure in accordance with the first dose distribution, the desired difference being determined on a basis of a predetermined dose fall-off gradient.

8. The system as defined in claim 7, wherein the predetermined dose fall-off gradient is specified by an operator of the system.

9. The system as defined in claim 7, wherein the predetermined dose fall-off gradient is pre-stored in the tangible, non-transitory computer readable storage medium.

10. The system as defined in claim 7, wherein the instructions, when executed by the computer device, further cause the computer device to carry out the check by executing a procedure for solving an optimization problem for determining the further dose distribution on a basis of a second dose distribution, the second dose distribution assigning a dose value to each voxel not belonging to the target structure, wherein the dose value is determined on a basis of the predetermined dose fall-off gradient.

11. The system as defined in claim 1, wherein the instructions, when executed by the computer device, further cause the computer device to determine the first dose distribution such that the radiation dose delivered to the target structure at least approximately corresponds to a minimum radiation dose required for fulfilling the treatment goals relating to the target structure.

12. The system as defined in claim 1, wherein the instructions, when executed by the computer device, further cause the computer device to determine minimum dose values for voxels belonging to the at least one structure at risk when said check is not affirmative, wherein the minimum dose values allow for determining a dose distribution such the mean radiation dose assigned to each shell in accordance with the dose distribution corresponds to the mean radiation dose assigned to the same shell in accordance with the first dose distribution.

13. The system as defined in claim 12, wherein the minimum dose values further allow for determining the dose distribution such that it includes dose values for voxels not belonging to the target structure or the at least one structure at risk, wherein the dose values do not exceed maximum dose values assigned to these voxels.

14. A method for assisting in planning a radiation therapy treatment of a region of a patient body on a basis of treatment goals comprising requirements for a radiation dose to be delivered to a target structure and to at least one structure at risk included in the region of the patient's body, the method comprising:

generating a treatment plan for the radiation therapy treatment only on the basis of the treatment goals relating to the target structure and obtaining a first dose distribution corresponding to the treatment plan, the treatment plan specifying optimized parameters for delivering the radiation therapy treatment, segmenting the region of the patient's body into a plurality of concentric shells surrounding the target structure and determining a mean radiation dose assigned to each shell in accordance with the first dose distribution, checking whether a further dose distribution can be determined, which fulfills the treatment goals relating to the at least one structure at risk, and which is configured such that the mean radiation dose assigned to each shell in accordance with the further dose distribution corresponds to the mean radiation dose assigned to a same shell in accordance with the first dose distribution, and indicating on a basis of a result of the check whether the treatment goals relating to the at least one target structure at risk are achievable.

15. A tangible, non-transitory computer readable medium that stores instructions, which, when executed by a computer device, causes the computer device to:

generate a treatment plan for a radiation therapy treatment only on a basis of treatment goals relating to a target structure and to obtain a first dose distribution corresponding to the treatment plan;

segment a region of a patient's body into a plurality of concentric shells surrounding the target structure and to determine a mean radiation dose assigned to each shell in accordance with the first dose distribution;

check whether a further dose distribution can be determined, which fulfills the treatment goals relating to at least one structure at risk and, said further dose distribution is configured such that the mean radiation dose assigned to each shell in accordance with the further dose distribution corresponds to the mean radiation dose assigned to a same shell in accordance with the first dose distribution; and indicate on a basis of a result of the check whether the treatment goals relating to the target structure are achievable.

16. The tangible, non-transitory computer readable medium of claim 15, wherein the instructions, when executed by the computer device, further causes the computer device to: carry out the check by executing a procedure for solving an optimization problem for determining the further dose distribution, wherein the check is affirmative when the execution of the procedure results in the determination of the further dose distribution.

17. The tangible, non-transitory computer readable medium of claim 15, wherein the instructions, when executed by the computer device, further causes the computer device to: indicate an achievability of the treatment goals relating to the at least one structure at risk when the check is affirmative.

18. The non-transitory computer readable medium of claim 15, wherein the instructions, when executed by the computer device, further causes the computer device to: generate the first dose distribution on a basis of a three-dimensional image of a region of the patient's body composed of a plurality of voxels.

19. The tangible, non-transitory computer readable medium of claim 18, wherein the instructions, when executed by the computer device, further cause the computer device to: check whether the further dose distribution can be determined such that said further dose distribution includes dose values for voxels belonging to the at least one structure at risk, wherein the dose values do not exceed maximum dose values assigned to said voxels on a basis of treatment goals relating to the at least one structure at risk.

20. The tangible, non-transitory computer readable medium of claim 18, wherein the instructions, when executed by the computer device, further causes the computer device to: determine the first dose distribution such that a radiation dose delivered to the target structure at least approximately corresponds to a minimum radiation dose required for fulfilling the treatment goals relating to the target structure.

* * * * *